(12) United States Patent
Bergeron, Jr.

(10) Patent No.: US 6,492,489 B1
(45) Date of Patent: Dec. 10, 2002

(54) SYNTHETIC HYPUSINE PEPTIDES

(75) Inventor: Raymond J. Bergeron, Jr., Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/519,693

(22) Filed: Mar. 7, 2000

Related U.S. Application Data

(63) Continuation of application No. 09/136,472, filed on Aug. 19, 1998, now abandoned, and a continuation-in-part of application No. 09/136,270, filed on Aug. 19, 1998, now Pat. No. 6,248,866, which is a continuation-in-part of application No. 08/975,656, filed on Nov. 21, 1997, now abandoned, which is a continuation-in-part of application No. 08/962,300, filed on Oct. 31, 1997, now Pat. No. 5,973,113.

(51) Int. Cl.$^7$ .................................................. C07K 7/00
(52) U.S. Cl. ....................... 530/329; 530/328; 530/330; 514/16; 514/17; 562/553; 562/562
(58) Field of Search ................................. 562/553, 562; 530/328, 329, 330; 514/2, 16, 17

(56) References Cited

U.S. PATENT DOCUMENTS

| | | | |
|---|---|---|---|
| 5,344,846 A | 9/1994 | Jakus et al. | ................... 514/634 |
| 5,538,897 A | 7/1996 | Yates, III et al. | ............. 436/89 |

OTHER PUBLICATIONS

Bergeron, R.J., et al., "Synthesis of Reagents for the Construction of Hypusine and Deoxyhypusine Peptides and Their Application as Peptidic Antigens," *J. Med. Chem.*, 41(20):3888–3900 (1998).

Shiba, T., et al., "Hypusine, A New Amino Acid Occurring in Bovine Brain Isolation and Structural Determination," *Biochim. Biophys. Acta*, 244(3):523–531 (1971).

Imaoka, N. and Nakajima T., "Hypusine $N^6$—(4–Amino–2–Hydroxybutyl) –2,6–Diaminohexanoic Acid, In Tissue Proteins of Mammals," *Biochem. Biophys. Acta*, 320:97–103 (1973).

Park, M. H., et al., "Identification of Hypusine, an Unusual Amino Acid, in a Protein from Human Lymphocytes and of Spermidine as its Biosynthetic Precursor," *Proc. of the Nat. Acad. of Sci.*, 78(5):2869–2873 (1981).

Sano, A., et al., "Isolation and Identification of α–(γ–Aminobutyryl)—Hypusine," *J. of Neurochemistry*, 46(4):1046–1049 (1986).

Park, M. H., et al., "Eukaryotic Initiation Factor 4D Purification From Human Red Blood Cells and the Sequence of Amino Acids Around its Single Hypusine Residue," *J. of Bio. Chem.*, 261(31):14515–14519 (1986).

Sandholzer, U., et al., "cDNA and Derived Amino Acid Sequence of the Hypusine Containing Protein from *Dictyostelium discoideum*," *FEBS Letters*, 246, Issue 1–2:94–100 (1989).

Beninati, S., et al., "High–Performance Liquid Chromatographic Method for Determination of Hypusine and Deoxyhypusine," *Analytical Biochemistry* 184(1):16–20 (1990).

Ueno, S., et al., "Isolation and Identification of α– (β–alanyl) Hypusine from Bovine Brain," *Biochemica et Biophysica Acta*, 1073(1):233–235 (1991).

Bergeron, R.J. et.al., "Total Syntheses of (+)–Hypusine and Its (2S,9S)—Diastereomer," *J. Org. Chem.* 58:6804–6806 (1993).

Beyermann, M. et al., "Rapid Continuous Peptide Synthesis via FMOC Amino Acid Chloride Coupling and 4—(Aminomethyl)piperidine Deblocking," *J. Org. Chem.*, 55(2):721–728 (1990).

Martinez, J. et al., "On the Use of Carboxamidomethyl Esters (CAM Esters) in the Synthesis of Model Peptides. Scope and Limitations," *Tetrahedron*, 41(4):739–743 (1985).

Martinez, J. et al., "Carboxamidomethyl Esters (CAM Esters) as Carboxyl Protecting Groups," *Tetrahedron Letter.*, 24(47):5219–5222 (1983).

Moroder, L. et al., "A New Synthetic Route to Tyrosine–O–Sulfated Peptides: Synthesis of a Pancreaozymin–Caerulein–Hybrid Related Peptide," in *Hormone Receptors in Digestion and Nutrition*, G. Rosselin, et al. eds., Elsevier/North Holland Biomedical Press, Amsterdam, 129–135 (1979).

Moroder, L. et al., "Synthese von Tyrosin–O–sulfat–haltigen Peptiden," *Z. Physiol. Chem.*, 360:787–790 (1979).

Shioiri, T. et al., "Diphenylphosphoryl Azide. A New Convenient Reagent for a Modification Curtius Reaction and for the Peptide Synthesis," *J. Am. Chem. Soc.*, 94(17):6203–6205 (1972).

(List continued on next page.)

*Primary Examiner*—Christopher S. F. Low
*Assistant Examiner*—David Lukton
(74) *Attorney, Agent, or Firm*—Hamilton Brook Smith & Reynolds

(57) ABSTRACT

The invention relates to novel peptides synthesized according a method utilizing the hypusine reagent:

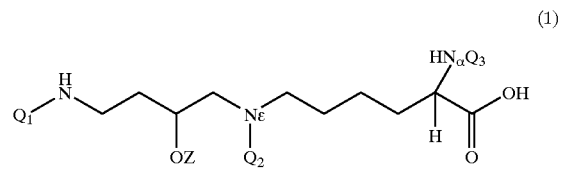

(1)

wherein:

$Q_1$ $Q_2$ and $Q_3$ may be the same or different and are amino protective groups, provided that $Q_3$ is orthogonal to $Q_1$ and $Q_2$; and Z is a hydroxy protective group, as well as improved methods of peptide synthesis wherein the above-described hypusine reagent is employed to prepare novel hypusine-containing peptides.

14 Claims, 3 Drawing Sheets

OTHER PUBLICATIONS

Wang, S.S. et al. "Cleavage and deprotection of peptides on MBHA–resin with hydrogen bromide," *Int. J. Peptide Protein Res.*, 40:344–349 (1992).

Yamashiro, D. et al., "The Use of $N^\alpha$, $N^{im}$–Bis (tert–butyloxycarbonyl) Histidine and $N^\alpha$–2–(p–Biphenylyl)isopropyloxycarbonyl–$N^{im}$–tert–butyloxy–carbonylhistidine in the Solid–Phase Synthesis of Histidine–Containing Peptides," *J. Am. Chem. Soc.*, 94(8):2855–2859 (1972).

Abbruzzese, A. et al., "Inhibition of deoxyhypusine hydroxylase by polyamines and by a deoxyhypusine peptide," *Biochim. Biophys, Acta*,997:248–255 (1989).

Bergeron, R.J. et al., "Development of a Hypusine Reagent for Peptide Synthesis," *J. Org. Chem.* 62(*10*):3285–3290 (1997).

Klier, H. et al., "Isolation and Structural Characterization of Different Isoforms of the Hypusine–Containing Protein eIF–5A from HeLa Cells," *Biochemistry* 34:14693 (1995).

Park, MH et al., "Hypusine: its post–translational formation in eukaryotic initiation factor 5A and its potential role in cellular regulation," *Biofactors* 4:95–104 (1993).

Bergeron et al., "Development of a Hypusine Reagent for Peptide Synthesis," *J. Org. Chem.* 62: 3285–3290 (1997).

Moroder, et al., "A New Synthetic Route to Tyrosine- -O-Sulfated Peptides: Syntehsis of a Pancreozymin-Caerulein-Hybrid Related Peptide," in *Hormone Receptors in Digestion and Nutrition*, G. Rosselin, et al., eds., Elsevier/North Holland Biomedical Press, Amsterdam, pp. 129–135 (1979).

Moroder, et al., "Synthese vonTyrosin-O-sulfat-haltigen Peptiden," *Z. Physiol. Chem.*, vol. 360, pp. 787–790 (1979).

Yamashiro, et al., "The Use of $N^\alpha$, $N^{im}$ –Bis (tert–butyloxycarbonyl) Histidine and $N^\alpha$, –2–(p–Biphenylyl) Isopropyloxycarbonyl–$N^{im}$–tert–butyloxy–carbonylhistidine in the Solid–Phase Synthesis of Histidine–Containing Peptides," *J. Am. Chem. Soc.*, vol. 94, pp. 2855–2859 (1972).

Park, M.H., et al., "Hypusine: its post–translational formation in eukaryotic initiation factor 5A and its potential role in cellular regulation," *Biofactors*, vol. 4, No. 2, pp. 95–104 (1995).

Mehta, et al., "Improved Efficiency and Selectivity in Peptide Synthesis: Use of Triethylsilane as a Carbocation Scavenger in Deprotection of t–Butyl Esters and t–Butoxycarbonyl–Protected Sites," *Tetrahedron Lett.*, vol. 33, pp. 5441–5444 (1992).

Stewart, et al., "Protection of the Hydroxyl Group in Peptide Synthesis," in *The Peptides*, Gross, et al., eds., Academic Press, New York, vol. 3, pp. 169–201 (1981).

Tarbell, et al., "New Method to Prepare N–t–Butoxycarbonyl Derivatives and the Corresponding Sulfur Analogs from di–t–Butyl Dicarbonate or di–t–Butyl Dithiol Dicarbonates and Amino Acids," *Proc. Natl. Acad. Sci. USA*, vol. 69, pp. 730–732 (1972).

Wang, et al., "Cleavage and Deprotection of Peptides on MBHA–Resin With Hydrogen Bromide," *Int. J. Peptide & Protein Res.*, vol. 40, pp. 344–349 (1992).

Beyermann, et al., "Rapid Continuous Peptide Synthesis via FMOC Amino Acid Chloride Coupling and 4–(Aminomethyl) piperidine Deblocking," *J. Org. Chem.*, vol. 55, pp. 721–728 (1990).

Martinez, et al., "On the Use of Carboxamidomethyl Esters (CAM Esters) in the Synthesis of Model Peptides. Scope and Limitations," *Tetrahedron*, vol. 41.

Martinez, et al., "Carboxamidomethyl Esters (CAM Esters) as Carboxyl Protecting Group," *Tetrahedron Lett.*, vol. 24, pp. 5219–5222 (1983).

Bernady, et al., "Prostaglandins and Congeners.20. Synthesis of Prostaglandins via Conjugate Addition of Lithium trans–1–Alkenyltrialkylalanate Reagents. A Novel Reagent for Conjugate 1,4–Additions," *J. Org. Chem.*, vol. 44, pp. 1438–1447 (1979).

Borch, et al., "The Cyanohydridoborate Anion as a Selective Reducing Agent," *J. Am. Chem. Soc.*.

SEQUENCE LISTING

```
<160> NUMBER OF SEQ ID NOS: 6

<210> SEQ ID NO 1
<211> LENGTH: 8
<212> TYPE: PRT
<213> ORGANISM: Homo sapiens
<220> FEATURE:
<221> NAME/KEY: SITE
<222> LOCATION: 3
<223> OTHER INFORMATION: Xaa = Hypusine

<400> SEQUENCE: 1

Thr Gly Xaa His Gly His Ala Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Example of peptides of invention
<220> FEATURE:
<221> NAME/KEY: SITE
<222> LOCATION: 7
<223> OTHER INFORMATION: Xaa = Hypusine
```

```
<400> SEQUENCE: 2

Ser Thr Ser Lys Thr Gly Xaa His Gly His Ala Lys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Example of peptides of invention
<220> FEATURE:
<221> NAME/KEY: SITE
<222> LOCATION: 4
<223> OTHER INFORMATION: Xaa = Hypusine

<400> SEQUENCE: 3

Cys Thr Gly Xaa His Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Example of peptides of invention
<220> FEATURE:
<221> NAME/KEY: SITE
<222> LOCATION: 3
<223> OTHER INFORMATION: Xaa = Hypusine

<400> SEQUENCE: 4

Thr Gly Xaa His Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Example of peptides of invention
<220> FEATURE:
<221> NAME/KEY: SITE
<222> LOCATION: 4
<223> OTHER INFORMATION: Xaa = Hypusine

<400> SEQUENCE: 5

Lys Thr Gly Xaa His Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Example of a peptide of the invention
<220> FEATURE:
<221> NAME/KEY: SITE
<222> LOCATION: 4
<223> OTHER INFORMATION: Xaa = Hypusine
<220> FEATURE:
<221> NAME/KEY: SITE
<222> LOCATION: 6
<223> OTHER INFORMATION: Xaa = Hydroxylated glycine

<400> SEQUENCE: 6

Cys Thr Gly Xaa His Xaa
1               5
```

SYNTHETIC HYPUSINE PEPTIDES

RELATED APPLICATION(S)

This application is a continuation of Ser. No. 09/136,472, filed Aug. 19, 1998, now abandoned, which is a continuation-in-part of Ser. No. 08/975,656, filed Nov. 21, 1997, now abandoned, and a continuation-in-part of Ser. No. 09/136,270, filed Aug. 19, 1998 now U.S. Pat. No. 6,248,866 which is a continuation-in-part of Ser. No. 08/962,300, filed Oct. 31, 1997, now U.S. Pat. No. 5,973,113, the entire teachings of which are incorporated herein by reference.

BACKGROUND OF THE INVENTION

Hypusine [$N_\epsilon$-(4-amino-2-hydroxybutyl) lysine], or [2S, 9R)-2, 11-diamino-9-hydroxy-7-azaundecanoic acid], an unusual naturally occurring amino acid, having the structure:

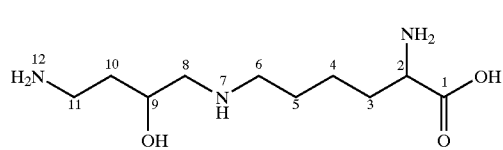

(A)

was first isolated from bovine brain extracts by Shiba et al. in 1971 [*Biochim. Biophys. Acta.* Vol. 244, pages 523–531 (1971)]. The molecule has two chiral centers at positions 2 and 9, each of which can be classified R or S by the Cahn-Ingold-Prelog method. The (2S, 9R) diastereomer (B), formed as a post-translational modification

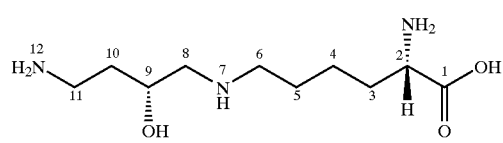

(B)

of lysine, has been shown to occur on a precursor protein of the eukaryotic initiation factor 5A (formerly called eIF-4D) [Cooper et al. *Proc. Natl. Acad. Sci. U.S.A.,* Vol. 80, pages 1854–1857 (1983); and Safer, *Eur. J. Biochem.,* Vol. 186, pages 1–3 (1989)]. This initiation factor 5A is unique in that it is the only known cellular protein that contains the amino acid hypusine (Hpu). In the mid-1970's eIF-5A was shown to stimulate ribosomal subunit joining and to enhance 80 S-bound Met-t-RNA$_i$ reactivity with puromycin [Anderson et al., *FEBS Lett.,* Vol. 76, pages 1–10 (1977); and Kemper et al., *J. Biol. Chem.,* Vol. 251, pages 5551–5557 (1976)]. Later, in 1983, Cooper et al., supra, suggested that a hypusine-modified protein serves as an important initiation factor in all growing eukaryotic cells. In 1986, Park et al.,*J. Biol. Chem.,* Vol. 261, pages 14515–14519 (1986)] isolated the eIF-5A protein from human red blood cells and elucidated the amino acid sequences surrounding the single hypusine residue, as Thr-Gly-Hpu-His-Gly-His-Ala-Lys (SEQ ID NO: 1). Furthermore, and most interesting because of the potential application to the control of HIV replication [Bevec et al.,*J. Proc. Natl. Acad. Sci. U.S.A.,* Vol. 91, pages 10829–10833 (1994); and Ruhl et al.,*J. Cell Biol.,* Vol. 123, pages 1309–1320 (1994)], the synthesis of eIF-5A analogues are of great therapeutic significance.

Since hypusine is specific to eIF-5A, antibodies derived from hypusine-containing peptides could be used to quantitate the levels of eIF-5A directly and with high specificity. Interest in developing an antibody assay of eIF-5A to investigate the physiological role of this important initiation factor prompter total synthesis of hypusine and its (2S, 9R)-diastereomer [Bergeron et al., *J. Org. Chem.,* Vol. 58, pages 6804–6806 (1993)]. The key step in the synthesis involved the $N_\epsilon$-alkylation of $N_\epsilon$-benzyl-$N_\alpha$-carbobenzyloxy-(L)-lysine benzyl ester with (R)- or (S)-epichlorohydrin to give the respective (2S, 9R)- and (2S, 9S)-chlorohydrins. Subsequent displacement of the respective chlorides by cyanide ion provided the protected hypusine skeletons. The final step, hydrogenation over $PtO_2$ in AcOH, followed by neutralization and re-acidification, yielded the respective (2S, 9S)- and (2S, 9R)-hypusine dihydrochlorides. A comparison of the reported hypusine optical rotation with that of the synthetic (2S, 9R)-hypusine B confirmed the stereochemical integrity of both chiral centers throughout the synthesis.

Synthetic methodology for accessing hypusine itself exists and it was desirable to have a selectively-protected hypusine reagent which could be used to incorporate this unusual amino acid into selected peptides. Copending application Ser. No. 08/962,300, filed Oct. 31, 1997 now U.S. Pat. No. 5,973,113 entitled "Hypusine Reagent for Peptide Synthesis," the entire contents and disclosure of which are incorporated herein by reference, describes a selectively protected hypusine reagent useful for incorporating hypusine into peptides, as well as methods for preparation of the hypusine reagent.

It is an object of the present invention to provide novel hypusine-containing peptides, as well as methods for their synthesis utilizing the above-described hypusine reagent.

SUMMARY OF THE INVENTION

The above and other objects are realized by the present invention, one embodiment of which relates to novel peptides containing the hypusine moiety.

More specifically, the present invention relates to novel hypusine-containing peptides synthesized utilizing the hypusine reagent:

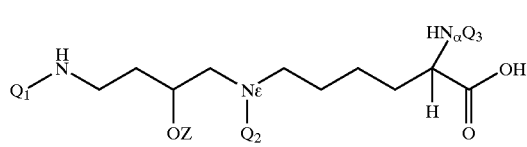

(1)

wherein:

$Q_1$, $Q_2$ and $Q_3$ may be the same or different and are amino protective groups, provided that $Q_3$ is orthogonal to $Q_1$ and $Q_2$; and Z is a hydroxy protective group.

A further embodiment of the invention relates to compounds of structure (2) which may be synthesized using hypusine reagent (1), wherein Hpu is the hypusine amino acid residue, S and T are each independently peptide residues from zero to about 12 amino acids in length. Compounds of the invention find utility in the study of biochemical processes involving hypusine.

Another embodiment of the invention concerns improved methods of peptide synthesis wherein the above-described hypusine reagent is employed to prepare novel hypusine-containing peptides.

BRIEF DESCRIPTION OF THE DRAWINGS

FIGS. 1 and 2 correspond to the chemistry described in Examples 1 through 8.

DETAILED DESCRIPTION OF THE INVENTION

Figure 1:
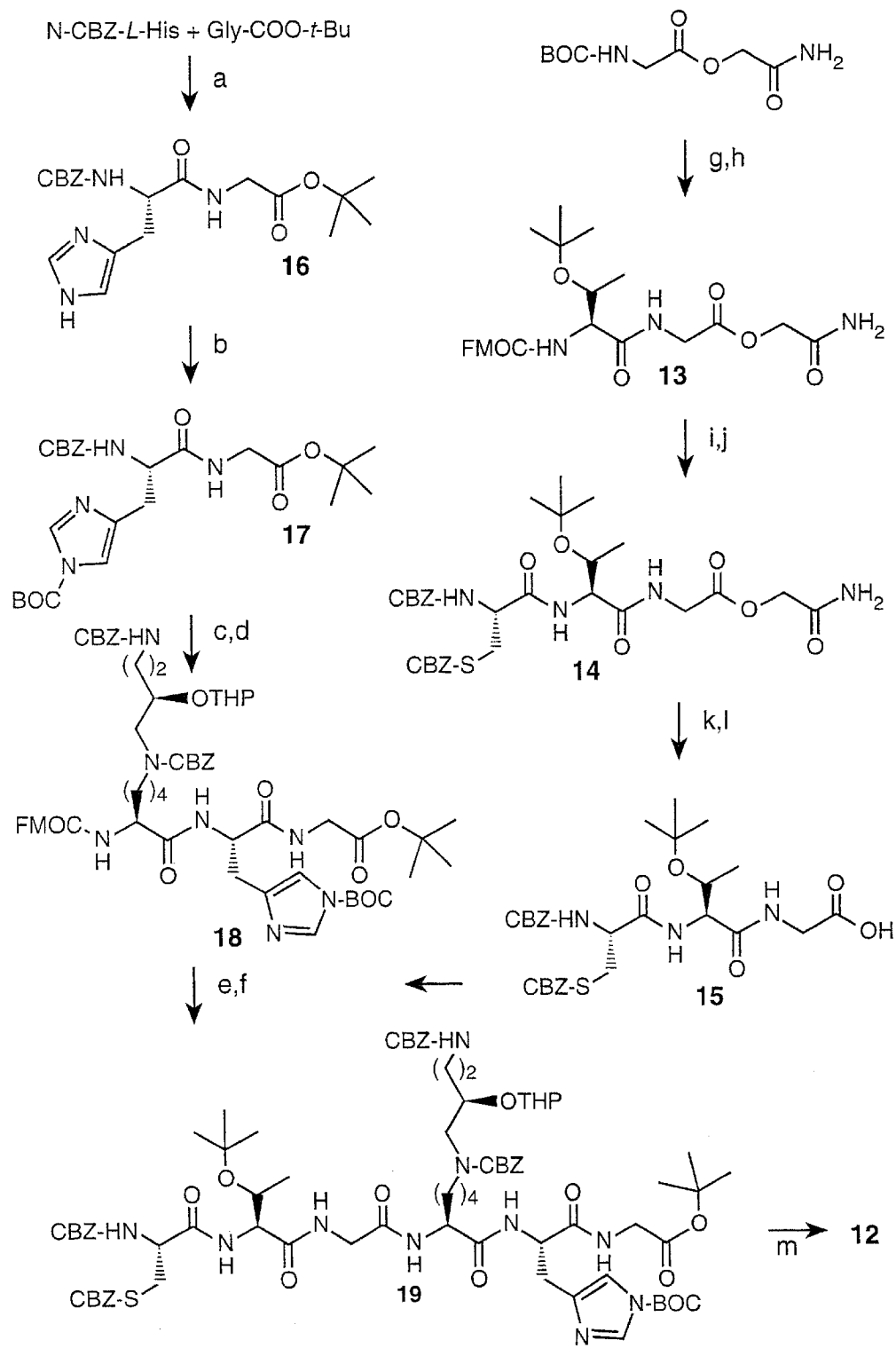
FIGS. 1 and 2 depict example reaction schemes for preparing peptides of the invention.

The method for synthesizing the hypusine reagent comprises:

a. providing an ester of $N_\epsilon$-, $N_\alpha$-diprotected L-lysine, the ester having the formula:

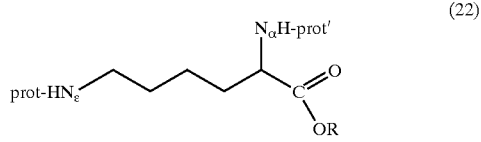
(22)

wherein prot and prot' are N-protective groups which are mutually orthogonal and R is the residue of an esterifying alcohol which is orthogonal with respect to prot and prot', b. removing prot from $N_\epsilon$ of (22) and converting the product to a compound of the formula:

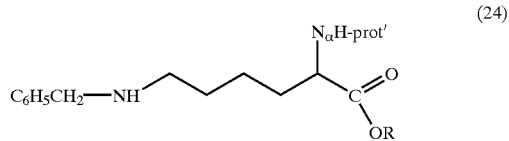
(24)

c. converting (24) to a chlorohydrin of the formula:

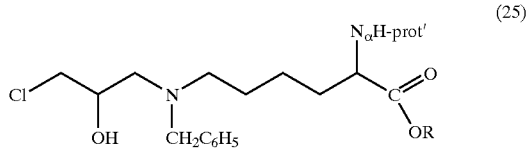
(25)

d. displacing the Cl group of (25) with CN to produce a nitrile of the formula:

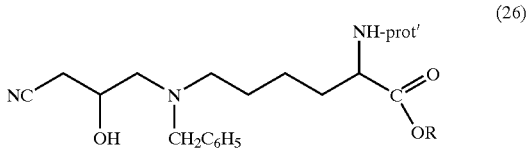
(26)

e. debenzylating the $N_\epsilon$ group and converting the CN group of (26) to an amine group to produce an amino alcohol of the formula:

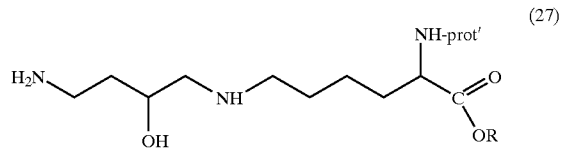
(27)

f. acylating the free amino groups of (27) to provide a di-N-protected $N_\alpha$-protected L-lysine ester of the formula:

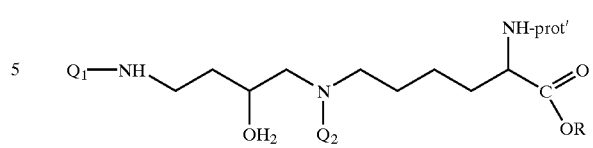
(28)

g. removing R and prot' from (28) to produce a compound of the formula:

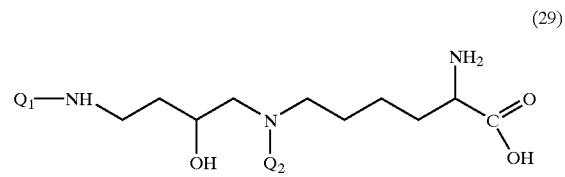
(29)

and h. acylating the free amino group and protecting the OH group to produce the hypusine derivative (1).

The expression "amino protective group" as used herein is intended to designate groups ($Q_1$, $Q_2$ and $Q_3$) which are inserted in place of a hydrogen atom of an amino group or groups in order to protect the amino group(s) during synthesis.

Selection of a suitable amino protecting group will depend upon the reason for protection and the ultimate use of the protected product. When the protecting group is used solely for protection during synthesis, then a conventional amino protecting group may be employed. Appropriate amino protecting groups are known in the art and are described, for example, by Bodanszky in Principles of Synthesis, Springer-Verlag, N.Y. (1984); by Ives in U.S. Pat. No. 4,619,915; and in the various publications on peptide chemistry referred to in the latter. See also *Methoden der Organischen Chemie,* Houben-Weyl, Vol. 15, No. 1, for protecting groups and Vol. 15, No. 2, for methods of peptide synthesis. Representative amino protecting groups for synthetic use include acyl groups such as tert-butoxycarbonyl, benzyloxycarbonyl, fluorenylmethoxycarbonyl (FMOC), benzoyl, acetyl and the like. Yet other conventional amino protecting groups for use in synthesis are described in the literature [Bodanszky, supra, and Ives, supra].

The expression "hydroxyl protective group" as used herein is intended to designate a group (Z) which is inserted in place of a hydrogen atom of an OH group or groups in order to protect the OH group(s) during synthesis.

The preferred hydroxyl protective groups are the ethers, with the most preferred being the tetrahydropyranyl ether.

The term "orthogonal" when used herein to modify the term "protective group(s)" is intended to designate those protective groups in the molecule which are capable of being selectively removed from the molecule in the presence of other protective groups in the molecule without affecting the latter.

The various protecting groups for hydroxyl and amino functions discussed above can be substituted for the hydroxyl and amino functions in the instant amino acids/peptides (or their precursor molecules) by methods well known in the art. Methods for chemical removal of the protecting groups (when such are not to be retained in the pharmaceutically useful end product) are likewise well known to the skilled artisan. Typically, amine protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups which are incorporated in the pharmaceutical end product must be amenable to hydrolytic or metabolic cleavage in vivo.

Inspection of the structure of hypusine (A) reveals five potentially reactive centers: two primary amino and one secondary amino groups, a secondary hydroxyl group and a carboxyl group. In eIF-5A, the α-amino nitrogen (N2) required a protecting group which was orthogonal, i.e., removable under conditions different from those under which the groups masking N7 and N12 are removed, to those masking the other two potentially reactive amines (N7 and N12). Therefore, the N2 nitrogen was protected as, e.g., the N-FMOC derivative, while the N7 and N12 amines were protected as, e.g., the N-CBZ moieties. The 9-hydroxyl was masked as, e.g., a tetrahydropyranylether. This protection was necessary as the poorly reactive secondary hydroxyl was expected to cause difficulty with the anticipated N-acylating agents used in solid phase synthesis [Stewart, *The Peptides,* Vol. 3, page 170, Gross et al., eds., Academic Press, New York (1981)].

Figure 3:
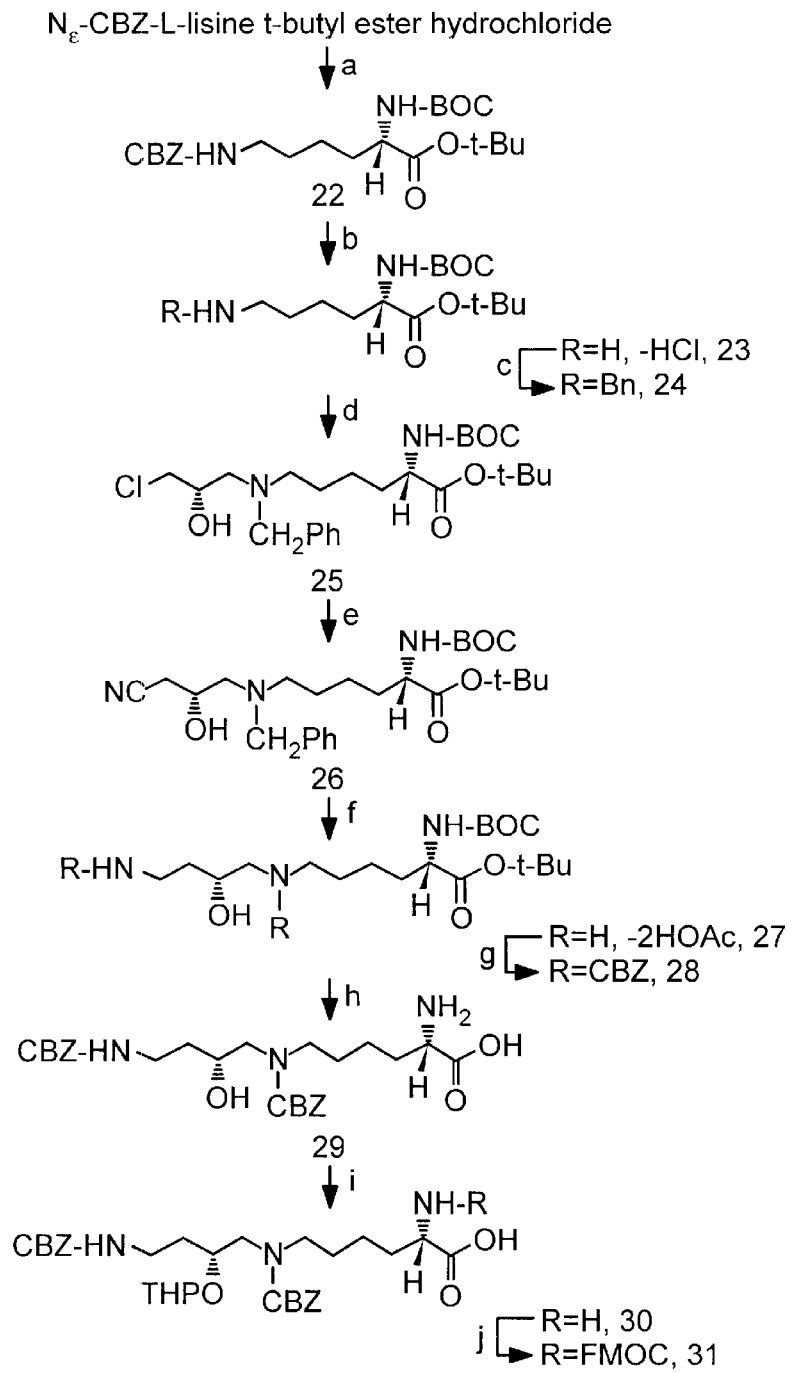
FIG. 3 is a depiction of a reaction scheme for synthesizing the hypusine reagent of the invention.

As shown in FIG. 3, the synthesis preferably begins with the t-butoxycarbonylation of $N_\epsilon$-CBZ-L-lysine t-Bu ester to give (22) in 98% yield [Tarbell et al., *Proc. Natl. Acad. Sci. USA,* Vol. 69, pages 730–732 (1972)].

The $N_\epsilon$-CBZ group of (22) was removed by hydrogenation over 10% Pd-C in ethanol and aqueous HCl to give 23 in 99% yield [Bergmann et al., *Ber. Dtsch., Chem. Abs.,* Vol. 65, pages 1192–1201 (1932)]. The $N_\epsilon$-benzyl-$N_\alpha$-BOC-L-lysine t-Bu ester (24) was synthesized from (23) by reductive amination of the liberated $N_\epsilon$ amine with benzaldehyde and sodium cyanoborohydride [Borch et al., *J. Am. Chem. Soc.,* Vol. 93, pages 2897–2904 (1971)].

The earlier synthesis of hypusine [Bergeron et al., supra] developed a chiral 4-amino-2-hydroxy butane synthon for accessing the parent molecule from an L-lysine derivative. In particular, this fragment made it possible to elaborate the $N_\epsilon$ benzyl group of a protected L-lysine into the N7-N12 structure of hypusine. In the synthesis of the present invention, this concept is further exploited. As shown in the reaction scheme depicted in FIG. 3, the subsequent $N_\epsilon$-alkylation of (24) with (S)-epichlorohydrin gave the (2S, 9S)-chlorohydrin (25). Displacement of the chloride in (25) by cyanide ion afforded the protected (2S, 9R)-hypusine skeleton (26). Debenzylation at N7 and conversion of the terminal nitrile in (26) was accomplished by hydrogenation to give the amino alcohol (27) as a diacetate. Acylation of the amino functions of amino alcohol (27) at N7 and N12 using CBZ groups as protecting groups provided di-CBZ-$N_\alpha$-t-BOC-(L)-lysine t-butyl ester (28). Selective removal of the t-butyl ester and $N_\alpha$-BOC protecting groups was accomplished with TFA and triethylsilane [Mehta et al., *Tetrahedron Lett.,* Vol. 33, pages 5441–5444 (1992)] to give the di-CBZ derivative (29). The secondary 9-hydroxyl function was protected as tetrahydropyranylether (30) [Bernady et al., *J. Org. Chem.,* Vol. 44, pages 1438–1447 (1979)] and subsequent acylation of the remaining $N_\alpha$-amine function with 9-fluorenylmethyl N-succinimidyl carbonate gave the hypusine reagent (31) with the desired protecting groups. Reagent (31) was converted to the dihydrochloride salt of (2S, 9R)-hypusine to give identical $^1$H NMR and comparable optical rotation was cited in the art [Bergeron et al., supra] by removing the FMOC group with 4-aminomethyl-piperidine [Beyermann et al., *J. Org. Chem.,* Vol. 55, pages 721–728 (1990)] and de-protection of the remaining protecting groups following a method by Wang et al. [*Int. J. Peptide Res.,* Vol. 40, pages 344–349 (1992)].

In a similar fashion, hypusine reagent molecules of differing stereochemistries may be obtained in a like manner employing starting materials of opposite stereochemistries such as (R)-epichlorohydrin.

The novel peptides (2) of the present invention comprise any synthetic peptide that incorporates within its structure the hypusine moiety, which is synthesized according to a method involving the use of the above-described hypusine reagent (1).

In compounds of structure (2), S and T are peptide residues from zero to about 12 amino acids in length, and preferably, are peptide residues from zero to about six amino acids in length. Most preferably, S and T are peptides residues from zero to about three amino acids in length S and T may vary independently in length and in composition of amino acid residues. The terminal amino acid reside of T may be hydroxylated. Non-limiting examples of peptides of the invention area:

L-Ser-L-Thr-L-Ser-L-Lys-L-Thr-Gly-Hpu-L-His-Gly-L-His-L-Ala-L-Lys (SEQ ID NO: 2),

L-Cys-L-Thr-Gly-Hpu-L-His-Gly (SEQ ID NO: 3),

L-Cys-L-Thr-Gly-Hpu-L-His-Gly-OH (SEQ ID NO:6),

Hpu-L-His-Gly,

L-Thr-Gly-Hpu-L-His-Gly (SEQ ID NO: 4),

L-Lys-L-Thr-Gly-Hpu-L-His-Gly (SEQ ID NO: 5), wherein the Hpu linkage is the (2S, 9R)-diastereomer thereof.

Compounds of the invention find utility in the study of biochemical processes involving hypusine, such as in the study of transport mechanisms for eIF5A.

The peptides of the invention may be prepared employing conventional steps of peptide synthesis except that the above-described hypusine reagent (1) is employed to incorporate the hypusine moiety into the peptide chain. Conventional peptide synthesis steps are disclosed, for example, in Moroder et al., "Hormonal Receptors in Digestive Tract Physiology," G. Rosselin et al., eds., Elsevier/North-Holland Biomedical Press, Amsterdam, pages 129–135 (1979); and Moroder et al., *Z. Physiol. Chem.* Vol. 360, pages 787–790 (1979).

The synthesis of peptides is generally carried out through the condensation of the carboxyl group of an amino acid, and the amino group of another amino acid, to form a peptide bond. A sequence can be constructed by repeating the condensation of individual amino acid residues in stepwise elongation or, in some cases, by condensation between two pre-formed peptide fragments (fragment condensation). In such condensations, the amino and carboxy groups that are not to participate in the reaction must be blocked with protecting groups which should be readily introduced, be stable to the condensation reactions and be removed selectively from the completed peptide. If a peptide involves amino acids with side chains that may react during condensation, the problem of protection becomes increasingly difficult. A great range of reactive groups and side chains (amino, carboxy, thiol, hydroxy and the like) must be adequately blocked. Their blocking must be stable to unmasking of the α-amino or α-carboxy block for stepwise condensation and must be readily removed at the final stage, leaving the completed peptide moiety intact.

Several methods are known wherein peptides are synthesized in vitro. The principal methodology used for peptide synthesis involves variations of the solid-phase methodology developed by Merrifield et al. See, for example, Erickson et al., "The Proteins," third edition, Vol. 2, Chapter 3, Academic Press, New York (1976). Solid phase peptide synthesis involves attachment of a first amino acid to a solid support, such as a resin, followed by sequential addition of subsequent amino acids which results in assembly of the peptide chain on the solid support.

Peptides can also be synthesized by related methods involving coupling peptide fragments to solid supports as discussed by Erickson et al., supra, pages 268–269. This technique involves the synthesis of small peptide segments containing a few amino acids, which segments are then coupled to each other using fragment condensation techniques to form larger peptides. Fragment condensation techniques can be combined with standard solid phase techniques wherein small peptides are attached to resins followed by sequential attachment of single amino acids or other peptide segments. Alternatively, sequential attachment of small peptides to single resin-bound amino acids can also be accomplished. The combination of the two approaches provides flexibility to synthetic schemes.

Upon completion of a particular synthesis, the synthesized peptide is then removed from the resin, usually by chemical means such as treatment with hydrofluoric acid (HF). The chemical treatment also removes various amino acid and peptide protecting groups, such as CBZ, t-BOC or tosyl, which mask the reactivity of amino acid functional groups during synthesis.

In most peptide syntheses, the initial attachment to the resin involves the C-terminal amino acid of the peptide to be synthesized, which amino acid is covalently attached to the resin through an ester or amide linkage involving its α-carboxyl group. Synthesis then proceeds from the C- to the N-terminal. N-terminal to C-terminal peptide synthesis is less frequently used because the chemistry is more difficult and unwanted side reactions are more common.

The first amino acid may be covalently attached to the resin, in some cases, through its functional side chain. Initial attachment of an amino acid to the resin by means of the side chain functional group allows the possibility of bi-directional synthesis starting with the attached amino acid. Bi-directional synthesis cannot be performed if the initial amino acid is attached through the α-COOH or α-NH$_2$ group. Side chain functional groups which have been used for attachment to resins include the sulfhydryl group of cysteine, the imidazole group of histidine, the δ-amino group of ornithine, the ε-amino group of lysine and the γ-carboxyl group of glutamic acid. A review of the chemistry of solid phase peptide synthesis, including attachment of amino acids to resins via the α-COOH, α-NH and functional side chain groups, is found in Erickson et al., supra.

By using the insoluble resin support, it is possible to isolate the product of each coupling reaction simply by filtering the resin and washing it free of by-products and excess starting materials. In fact, the synthetic processes are so simplified and the time required for one cycle is so shortened that in recent years, it has become quite common to use automated peptide synthesizers. [See, for example, Barany et al., "The Peptides," Vol. 2, Academic Press, Inc., New York (1979), pages 1–284; or Kemp-Vellaccio, "Organic Chemistry," pages 1030–1032 (1980).]

Although the hypusine reagent described herein may be employed to access any hypusine-containing peptide, the method of the invention will be illustrated with reference to the following syntheses. It will be understood that any conventional peptide synthesis may be modified to prepare a hypusine-containing peptide by simply utilizing the herein described hypusine reagent at any convenient stage thereof.

While the hypusine reagent allows for the assembly of a variety of hypusine-containing peptides, the hypusine-containing pentapeptide found in eIF-5A capped at its N-terminus with L-Cys, i.e., L-Cys-Thr-Gly-Hpu-His-Gly (SEQ ID NO: 3) is a typical target peptide. The L-Cys, which is not contained in the natural peptide, was fixed to the sequence with the idea of being able to covalently link the peptide via a disulfide bond to a larger protein, in order to ultimately generate antibodies. The solution synthesis, a convergent approach, was carried out by elaborating from the C- to the N-terminus, as shown in FIG. 1, and involved the coupling of three appropriately-protected pieces: Cys-Thr-Gly, Hpu and His-Gly.

The carboxyamidomethyl (CAM) ester developed by Martinez et al., [Tetrahedron, Vol. 41, pages 739–743 (1985); and Tetrahedron Lett., Vol. 47, pages 5219–5222 (1983)] was employed as a carboxyl protecting group in generating the Cys-Thr-Gly fragment. This protecting group is orthogonal to the BOC, CBZ and FMOC groups. Thus, the synthesis of the masked Cys-Thr-Gly fragment 15 began with the N-BOC-Gly-CAM ester [Martinez et al., Tetrahedron, supra]. Removal of the BOC group with trifluoroacetic acid (TFA) gave the amine salt (60%) which was immediately coupled with N-FMOC-(O-t-butyl)-L-threonine to give the N-FMOC-(O-t-butyl)-L-Thr-Gly-CAM ester 13 in 85% yield. Treatment of 13 with 10% diethylamine (DEA) in DMF followed by coupling with N, S-di-CBZ-L-cysteine with BOP and DIEA afforded the N, S-di-CBZ-L-Cys-(O-t-butyl)-L-Thr-Gly-CAM ester 14 in 50% yield. Removal of the CAM ester with aqueous Na$_2$CO$_3$ followed by acidification with aqueous citric acid generated the N, S-di-CBZ-L-Cys-(O-t-butyl)-L-Thr-Gly acid 15 in 77% yield.

The design of the His-Gly fragment 17 was predicated on obtaining efficient coupling between the N$_\alpha$ His group and reagent 1. Previous work by Yamashiro et al., [J. Am. Chem. Soc., Vol. 94, pages 2855–2859 (1972)] demonstrated that t-butyl-carbonylation of the imidazole side chain prior to the condensation step substantially increased coupling yields between systems containing His residues and N-BOC groups. For this reason, the His-Gly fragment 17 was assembled in two steps. First, the condensation of glycine t-butyl ester and N$_\alpha$-CBZ-L-His with diphenyl-phosphorylazide (DPPA) [Shioiri et al., J. Am. Chem. Soc., Vol. 94, No. 17, pages 6203–6205 (1972)] afforded N$_\alpha$-CBZ-L-His-Gly t-butyl ester 16 (72%). In the second step, the His side chain was masked by the treatment with di-t-butyl dicarbonate in THF to give the N$_\alpha$-CBZ-N$_{im}$-BOC-L-His-Gly t-butyl ester 17 in 78% yield.

As shown in FIG. 1, the final hexapeptide 12 was constructed stepwise from the three aforementioned fragments, i.e., 1, 15 and 18. Hydrogenolysis of the N$_\alpha$-CBZ group of 17 provided the amine HCl salt (74%) which was condensed with hypusine reagent 1 to give the di-CBZ-THP protected Hpu-His-Gly tripeptide 18 in 85% yield. The amine generated by treatment of the N$_\alpha$-FMOC in 18 with 4-aminomethyl-piperidine (68%) [Beyermann et al., J. Org. Chem., Vol. 55, pages 721–728 (1990)] was acylated by the tripeptide acid 15 and BOP to give the masked conjugate 19 in 81% yield. The final deprotection of 19 with HBr/acetic acid in TFA and a "cocktail" of scavengers (phenol, pentamethylbenzene, triisopropylsilane, 1,2-ethanedithiol) at room temperature developed by Wang et al., [Int. J. Peptide. Res., Vol. 40, pages 344–349 (1992)] gave the Cys-Thr-Gly-Hpu-His-Gly (SEQ ID NO: 3) as its tetrakis-trifluoroacetic acid salt 12 in 22% yield. The peptide was fully assigned by DOCOSY, TOCSY and HMOC NMR.

Figure 2:
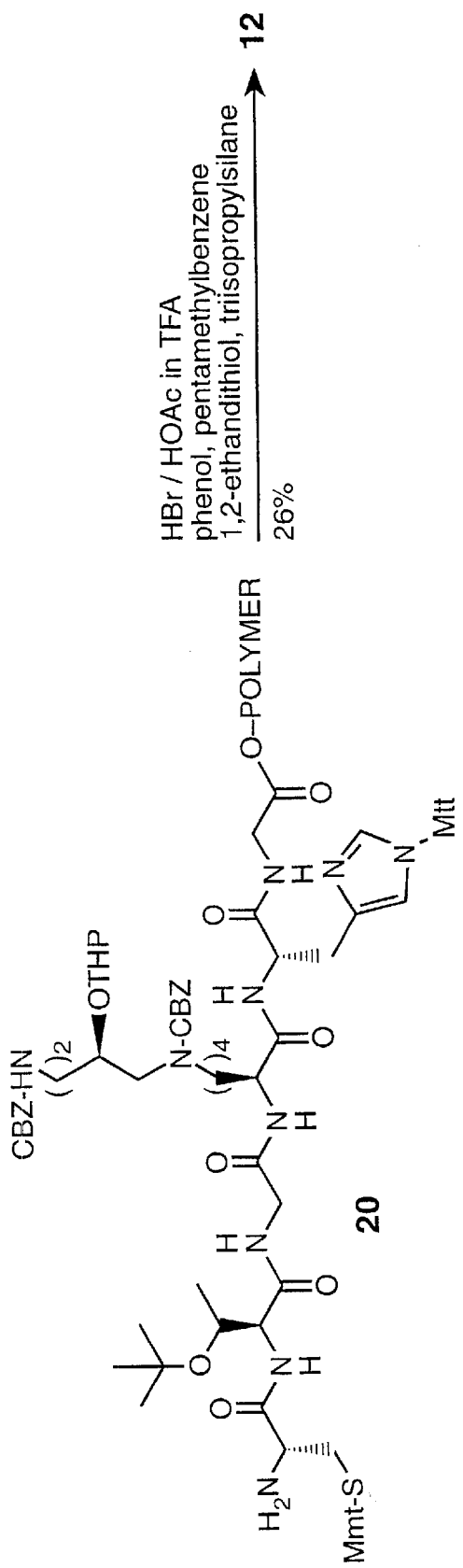

Polymer bounded synthesis of the hexapeptide 12 was performed on a HMP-resin [Want, supra] using an Applied Biosystems 432A Synthesizer. The Cys and His residues of the hexapeptide were initially protected with trityl groups while the Thr was protected as its t-butyl ether. Attempts to release the free hexapeptide by refluxing in TFA/phenol or with HBr/acetic acid in TFA with phenol and pentamethylbenzene, respectively, did not succeed. Use of the more labile 4-methoxytrityl and 4-methyltrityl groups to protect the Cys and His derivatives, respectively, produced the protected hexapeptide 20 (FIG. 2). Final deprotection of 20 was then achieved with HBr/acetic acid in TFA using a "cocktail" of four cation scavengers. This method generated very few side products and provided 12 after purification by HPLC in 24% yield. All analytical data were consistent with hexapeptide 12*4 TFA previously prepared by the solution-phase method.

In summary, the hypusine reagent described has been demonstrated to be a highly useful synthon in accessing the elF-5A pentapeptide sequence. While the yields are generally excellent for these kinds of systems, the most notable feature is the flexibility that this methodology offers in synthesizing related elF-5A mimics.

EXAMPLE 1

FMOC-Thr(O-t-butyl)-Gly Carboxyamido Methyl (CAM) Ester (14)

$N_\alpha$-BOC-Gly CAM ester [Martinez et al., *Tetrahedron*, supra] (1.16 g, 5.0 mmol) was dissolved in TFA (10 ml) and stirred 10 minutes at 0° C. The amine TFA salt was precipitated with diethyl ether (130 ml), filtered and dried (0.75 g, 60%). The amine salt (0.75 g) was then dissolved in a dry DMF (10 ml) solution containing FMOC-Thr (O-t-butyl)-OH (1.20 g, 3.0 mmol) and BOP (1.33 g, 3.0 mmol). The solution was cooled to 0° C., and diisopropylethylamine (DIEA, 1.15 ml, 6.6 mmol) was added dropwise. The solution was warmed to room temperature and stirred overnight. The volatiles were removed in vacuo, the resulting oil was dissolved in ethyl acetate (200 ml) and washed with 1 M citric acid, water, 5% aqueous $NaHCO_3$ solution and water. The organic layer was dried over $MgSO_4$ and concentrated. Flash chromatography (90% ethyl acetate/hexane) gave 14 as a colorless solid (1.30 g, 85%). $^1H$ NMR ($CDCl_3$) δ7.77(d, 2H, J=7.5 Hz), 7.65 (m, 1H), 7.60 (d, 2H, J=7.5 Hz), 7.45–7.27 (m, 4H), 6.60 (s br, 1H), 5.87 (d br, 1H), 5.54 (s br, 1H), 4.67 (m, 2H), 4.51–4.35 (m, 2H), 4.28–4.12 (m, 4H), 4.05 (m, 1H), 1.29 (s, 9H), 1.08 (d, 3H, J=6.4 Hz). Anal. calcd. for $C_{27}H_{33}N_3O_7$: C, 63.39; H, 6.50; N, 8.21. Found: C, 63.14; H, 6.60; N, 8.10. $[\alpha]^{22}_D$–0.8° (c=1.00, $CH_3OH$).

EXAMPLE 2

CBZ-Cys (CBZ)-Thr (O-t-butyl)-Gly Carboxyamidomethyl Ester (15)

A solution of 14 (0.46 g, 0.90 mmol) was dissolved in a solution of diethylamine (DEA, 0.8 ml) in dry DMF (8 ml). After stirring overnight at room temperature, the volatiles were removed in vacuo and the residue dissolved in 15 ml dry DMF. N, S-di-CBZ-L-Cys (0.35 g, 0.90 mmol) and BOP (0.40 g, 0.90 mmol) were added and the turbid solution cooled to 0° C. DIEA (0.25 g, 1.89 mmol) was added, and the solution was stirred at room temperature for 2 days. The reaction mixture was concentrated in vacuo, diluted with ethyl acetate (100 ml) and washed with 10% citric acid, water, 5% aqueous $NaHCO_3$ solution and water. The organic layer was dried over $MgSO_4$ and concentrated in vacuo. The resulting oil was purified by flash column chromatography (80% ethyl acetate/10% hexane/10% $CHCl_3$ to obtain 15 (0.29 g, 50%). mp 95–97° C. $^1H$ NMR ($CDCl_3$) δ7.70 (m, 1H), 7.28 (s, 10H), 6.78 (s, 1H), 6.00 (s, 1H), 5.50 (s, 1H), 5.23 (s, 2H), 5.17 (s, 2H), 4.62 (m, 2H), 4.41 (m, 1H), 4.30 (m, 1H) 4.25 (m, 1H), 4.15 (m, 1H), 3.94 (m, 1H), 3.30 (m, 2H), 1.65 (s, 1H), 1.20 (s, 9H), 1.07 (d, 3H). Anal. calcd. for $C_{31}H_{40}N_4O_{10}S$: C, 56.35; H, 6.10; N, 8.48. Found: C, 56.62; H, 6.14; N, 8.38. $[\alpha]^{25}_D$–14° (c=1.10, $CH_3OH$).

EXAMPLE 3

CBZ-Cys(CBZ)-Thr(O-t-butyl)-Gly-OH (16)

To a solution of 15 (0.90 g, 1.36 mmol) dissolved in DMF (14 ml) was added aqueous $Na_2CO_3$ (2.72 mmol, 8 ml) at room temperature. The solution warmed upon addition and water was added until the solution was clear. After 5 minutes, the pH was adjusted to 6 with citric acid (0.5 N, 9 ml). The reaction mixture was concentrated in vacuo; the residue was dissolved in ethyl acetate and washed with 0.5 N citric acid. The organic layer was dried over sodium sulfate and concentrated in vacuo. The residue was purified by column chromatography using LH-20 lipophilic Sephadex (50 g; eluting with 1% EtOH/toluene) to give 16 as a white solid (0.63 g, 77%). mp 124–125° C.; $^1H$ NMR ($CD_3OD$) δ7.39–7.25 (m, 10H), 5.24 (s, 2H), 5.12 (s, 2H), 4.46 (dd, 1H, J=8.6, 5.0 Hz), 4.33 (d, 1H, J=3.0 Hz), 4.16 (m, 1H), 3.92 (m, 2H), 3.45 (dd, 1H, J=14.3, 5.0 Hz), 3.16 (dd, 1H, J=14.3, 8.6 Hz), 1.20 (s, 9H), 1.09 (d, 3H, J=6.4 Hz). Anal. Calcd. for $C_{29}H_{37}N_3O_9S$: C, 57.70; H, 6.18; N, 6.96. Found: C, 57.76; H, 6.24; N, 7.02. $[\alpha]^{22}_D$+8.6° (c=0.50, $CHCl_3$).

EXAMPLE 4

CBZ-His-Gly-O-tert-Butyl (17)

Glycine t-butyl ester hydrochloride (2.20 g, 13.0 mmol) and $N_\alpha$-CBZ-L-His (3.44 g, 11.9 mmol) were dissolved in dry DMF (40 ml). The solution was cooled to 0° C. under an $N_2$ atmosphere, and diphenylphosphoryl azide (DPPA, 3.58 g, 13.0 mmol) was added dropwise over 5 minutes. The clear solution was stirred for 10 minutes and turned turbid upon addition of triethylamine (2.63 g, 26 mmol). The solution was stirred at room temperature overnight. The solution was concentrated and the residue purified by flash chromatography (8% EtOH/$CHCl_3$) to give 17 as a white solid (3.45 g, 72%). mp 64–66° C. $^1H$ NMR ($CD_3OD$) δ7.56 (d, 1H, J=1.1 Hz), 7.30 (m, 5H), 6.88 (s, 1H), 5.04 (m, 2H), 4.42 (m, 1H), 3.80 (m, 2H), 3.12 (m, 1H), 2.91 (m, 1H), 1.46 (s, 9H). Anal. calcd. for $C_{20}H_{26}N_4O_5$: C, 59.69; H, 6.51; N, 13.92. Found: C, 59.43; H, 6.46; N, 13.81.

EXAMPLE 5

CBZ-His(BOC)-Gly-O-tert-Butyl (18)

A solution of di-t-butyl dicarbonate (1.33 g, 6.0 mmol) in 3 ml THF was added dropwise at 0° C. to a solution of 17 (2.0 g, 5.0 mmol) in 15 ml THF. The reaction mixture was stirred overnight at room temperature and concentrated in vacuo. The residue was purified by flash chromatography (60% ethyl acetate/hexane) to give 1.96 g of 18 (78%). $^1H$ NMR ($CDCl_3$) δ8.00 (s, 1H), 7.30 (m, 6H), 6.60 (m, 1H), 5.10 (s, 2H), 4.58 (m, 1H), 3.85 (m, 2H), 3.03 (m, 2H), 2.38 (s, 1H), 1.60 (s, 9H), 1.40 (s, 9H). Anal. Calcd. for $C_{20}H_{26}N_4O_5$: C, 59.75; H, 6.82; N, 11.15. Found: C, 59.69; H, 6.87; N, 11.09. $[\alpha]^{22}_D$–4.0° (c=1.00, $CH_3OH$).

EXAMPLE 6

FMOC-Hpu(N7,N12-di-CBZ, O9-THP)-His(BOC)-Gly-O-tert-Butyl (19)

To a solution of 18 (185 mg, 0.37 mmol) and 1 N CHI (370 μl) in ethanol (15 ml) was added 10% Pd—C (18 mg), and the reaction mixture was hydrogenated for 2.5 hours at room temperature. The reaction mixture was filtered through Celite, concentrated in vacuo and purified by flash chromatography (CHCl$_3$/EtOH=9:1) to give H-His-(BOC)-Gly-O-t-Bu hydrochloride (101 mg, 68%). A portion of this ammonium salt (69 mg, 0.17 mmol) and hypusine reagent 1 (134 mg, 0.17 mmol) were dissolved in 12 ml dry DMF. The solution was cooled to 0° C. and BOP (87 mg, 0.20 mmol) was added and stirred for 20 minutes. DIEA (47.5 mg, 0.37 mmol) was added dropwise at 0° C. and the solution warmed to room temperature and stirred overnight. The volatiles were removed under reduced pressure, and the residue was dissolved in ethyl acetate and washed with 5% aqueous NaHCO$_3$ solution and water. The organic layer was dried over MgSO$_4$ and concentrated in vacuo and the residue purified by flash chromatography (4% EtOH/CHCl$_3$) to give 19 as a colorless oil (165 mg, 85%). $^1$H NMR (600 MHz) (CD$_3$OD) δ7.86 (m, 1H), 7.70 (d, 2H, J=7.5 Hz), 7.58 (m, 2H), 7.31–7.11 (m, 15H), 5.00 (m, 2H), 4.92 (s, 2H), 4.60 (m, 1H), 4.50–4.32 (m, 1H), 4.30–4.26 (m, 2H), 4.08 (t, 1H, J=6.8 Hz), 3.90 (m, 1H), 3.86–3.52 (m, 5H), 3.38–2.76 (m, 8H), 1.70–1.12 (m, 14H), 1.40 (s, 9H), 1.28 (s, 9H). HRMS m/z calcd. for C$_{63}$H$_{80}$N$_7$O$_{14}$ 1158.5763; found 1158.5739. $[\alpha]^{26}{}_D$–1.5° (C=1.00, CHCl$_3$).

EXAMPLE 7

CBZ-Cys(CBZ)-Thr(O-t-Bu)-Gly-Hpu(N7,N12-di-CBZ, O9-THP)-His(BOC)-Gly-O-t-Bu (20)

4-(Aminomethyl)-piperidine (1.0 ml) was added to 19 (156 mg, 0.14 mmol) dissolved in CHCl$_3$ (10 ml). The clear solution was stirred for 2 hours at room temperature. An additional portion of 4-(aminomethyl)-piperidine (1.0 ml) was added and stirring was continued another 40 minutes. The reaction mixture was taken up in 50 ml CHCl$_3$ and extracted three times with phosphate buffer (pH=5.5, 75 ml each). The organic layer was dried over Na$_2$SO$_4$, concentrated and purified by flash chromatography on silica (10% MeOH/CHCl$_3$) to give H-Hpu (N7, N12-di-CBZ, O9-THP)-His(BOC)-Gly-O-t-Bu as a colorless oil (88 mg, 68%). A portion of the colorless oil (10 mg, 11 μmol) and 16 (7 mg, 11 μmol) in dry DMF (2 ml) was cooled to 0° C. BOP (6 mg, 12 μmol) was added and stirred for 30 minutes. Diisopropylethylamine (4.5 μl, 26 μmol) was added dropwise and the solution was warmed to room temperature and stirred overnight. The reaction mixture was concentrated in vacuo. The residue was dissolved in ethyl acetate (15 ml) and extracted with 5% aqueous NaHCO$_3$ solution (10 ml) and water (10 ml). The organic layer was concentrated under reduced pressure and the residue purified by flash chromatography (10% EtOH/CHCl$_3$; R$_f$=0.35) to give 20 as a colorless oil (13 mg, 81%). $^1$H NMR (600 MHz) (CD$_3$OD) δ7.99 (m, 1H), 7.28–7.14 (m, 21H), 5.17–5.07 (m, 2H), 5.06–4.88 (m, 6H), 4.58 (dd, 1H, J=9.0, 4.2 Hz), 4.51–4.32 (m, 2H), 4.26 (m, 1H), 4.14 (m, 1H), 4.10 (m, 1H), 4.08–3.98 (m, 2H), 3.86–3.58 (m, 6H), 3.40–2.94 (m, 8H), 2.88 (m, 1H), 1.70–0.94 (m, 17H), 1.48 (s, 9H), 1.34 (s, 9H), 1.08 (s, 9H). HRMS m/z calcd. for C$_{77}$H$_{105}$N$_{10}$O$_{20}$S 1521.7227; found 1521.736. $[\alpha]^{26}{}_D$–1.2° (c=1.00, CHCl$_3$).

EXAMPLE 8

Cys-Thr-Gly-Hpu-His-Gly (SEQ ID NO: 3), Trifluoroacetic Acid Salt (12)

Method (a)

A solution of 20 (13 mg, 7.2 μmol) and phenol (5 mg, 50 μmol) was heated to reflux for 90 minutes in degassed TFA (5.0 ml) under an argon atmosphere. The reaction mixture was concentrated in vacuo and the residue applied to a C-18 plug (Supelco; water/acetonitrile=88/22+0.1% TFA). Further purification was performed by preparative HPLC (solvent systems A, aqueous 0.1% TFA; and B, 0.1% FA in CH$_3$CN; linear gradient of 0–20% B in 50 minutes; flow rate 4.0 ml/minute; detection at 214 nm; retention time=8.4 minutes) using a C-18 reverse phase column (Dynamax 300 A C$_{16}$) to give 12 as a colorless oil (2 mg, 24%). $^1$H NMR (D$_2$O) (600 MHz) δ8.69 (d, 1H, J=1.2 Hz), 7.38 (s, 1H), 4.80 (m, 1H), 4.49 (d, 1H, J=4.9 Hz), 4.41 (t, 1H, J=5.6 Hz), 4.36 (dd, 1H, J=8.5, 6.0 Hz), 4.29 (m, 1H), 4.11 (m, 1H), 4.09–4.00 (m, 4H), 3.37 (dd, 1H, J=15.5, 7.2 Hz), 3.29–3.06 (m, 9H), 1.99 (m, 1H), 1.86 (m, 2H), 1.76 (m, 3H), 1.45 (m, 2H), 1.32 (d, 3H, J=6.4 Hz). MS (MALDI-Tof) m/z calcd. for C$_{27}$H$_{48}$N$_{10}$O$_9$S 688.33 (M$^{30}$), found 688.96.

Method (b)

The polymer-bound peptide 21 was synthesized using an Applied Biosystems 432A Synthesizer. Amino acid analysis for 21: Gly 2.09, His 1.03, Thr 0.88. An aliquot of 21 (49 mg, 19.3 μmol), phenol (250 mg) and pentamethylbenzene (250 mg) were dissolved in degassed TFA (5.0 ml) at 0° C. Saturated HBr in acetic acid solution (0.2 ml), triisopropylsilane (0.1 ml) and 1,2-ethanedithiol (0.1 ml) were added under an argon atmosphere. The solution was stirred at room temperature for 1 hour and concentrated under reduced pressure. The residue was dissolved in 10% acetic acid (10 ml) and extracted with methyl tert-butyl ether (3×25 ml). The aqueous layer was concentrated in vacuo and the residue was purified on a preparative HPLC as in method (a) above using a C-18 reverse phase column (Dynamax 300 A C$_{18}$) to give 12 as a colorless oil (5.2 mg, 24%). $^1$H NMR and MS analytical data were identical to those for 12 prepared by method (a) above. $[\alpha]^{26}{}_D$–16 7° (c=0.30, H$_2$O). Amino acid analysis: Gly 1.94, His 1.02, Thr 1.04.

EXAMPLE 9

N$_\alpha$-BOC-N$_\epsilon$-CBZ-L-Lysine tert-Butyl Ester (22)

Sodium hydrogencarbonate (2.81 g, 33.47 mmol) in water (75 ml) was added to H-Lys(CBZ)-O-t-Bu hydrochloride (12.00 g, 32.18 mmol) in chloroform (100 ml) and the mixture was stirred at room temperature for 5 minutes under an N$_2$ atmosphere. Di-tert-butyl dicarbonate (7.02 g, 32.18 mmol) in chloroform (50 ml) was added, the mixture refluxed for 1.5 hours and allowed to cool to room temperature. The layers were separated, the aqueous layer extracted with chloroform (3×100 ml) and the combined organic layers dried over magnesium sulfate. Concentration in vacuo followed by flash chromatography (3:1 hexane:ethyl acetate) gave (22) (13.82 g, 98%) as a colorless oil. $^1$H NMR (CDCl$_3$) δ7.30 (s, 5H), 5.10 (s, 2H), 4.82 (m, 1H), 4.18 (m, 1H), 3.20 (m, 2H), 1.90–1.30 (m, 6H), 1.48 (s, 9H), 1.46 (s, 9H); $^{13}$C NMR (CD$_3$OD) δ173.8, 158.8, 158.1, 138.4, 129.4, 128.9, 128.7, 82.5, 80.4, 67.3, 55.7, 41.4, 32.4, 30.4, 28.7, 28.3, 24.0. HRMS m/z calcd. for C$_{23}$H$_{37}$N$_2$O$_6$ 437.2652, found 437.2643. Anal. calcd. for C$_{23}$H$_{36}$N$_2$O$_6$: C, 63.28; H, 8.31; N, 6.42. Found: C, 63.13; H, 8.28; N, 6.47. $[\alpha]^{27}{}_D$+5.0 (c=2.00, CHCl$_3$).

EXAMPLE 10

N$_\alpha$-BOC-L-Lysine tert-Butyl Ester Hydrochloride (23)

N$_\alpha$-BOC-N$_\epsilon$-CBZ-L-lysine tert-butyl ester (22) (34.51 g, 79.15 mmol) was dissolved in a mixture of 300 ml absolute EtOH and 1 N HCl (88 ml). Prior to the introduction of H$_2$ gas, 10% Pd—C (2.95 g) was added. After 7 hours, additional catalyst (1.0 g) was added. After 5 hours, the black suspension was filtered through a bed of Celite and washed with EtOH. The filtrate was concentrated and the residue dried under high vacuum to give the N$_\alpha$-BOC-L-lysine tert-butyl ester as its hydrochloride salt (23) (26.59 g, 99%). $^1$H NMR (CD$_3$OD) δ3.95 (dd, 1H, J=8.8, 5.0 Hz), 2.93 (t, 2H, J=7.7 Hz), 1.84–1.60 (m, 6H), 1.45 (s, 9H), 1.43 (s, 9H); $^{13}$C NMR (CD$_3$OD) δ173.5, 158.2, 82.7, 80.5, 79.5, 55.5, 40.6, 32.1, 28.7, 28.3, 23.9. HRMS m/z calcd. for C$_{15}$H$_{31}$N$_2$O$_4$ 303.2284, found 303.2272. [α]$^{26}_D$ −10.1° (c=1.00, CH$_3$OH).

EXAMPLE 11

N$_\epsilon$-Benzyl-N$_\alpha$-BOC-L-Lysine tert-Butyl Ester (24)

N$_\alpha$-BOC-L-lysine t-butyl ester hydrochloride salt (23) (25.97 g, 76.64 mmol) was dissolved in CHCl$_3$ (300 ml) and washed with saturated aqueous Na$_2$CO$_3$ solution (2×100 ml). The organic layer was separated, dried (MgSO$_4$), filtered and concentrated. The resultant oil (the free amine) was combined with benzaldehyde (10.42 g, 98.13 mmol), EtOH (150 ml) and activated 3 Å molecular sieves (46.0 g). The mixture was stirred under N$_2$ for 6 hours. Sodium cyanoborohydride (2.41 g, 38.4 mmol) was added and the mixture was stirred overnight at room temperature. The brown mixture was filtered and the filtrate acidified to pH 2 with 1 N HCl (110 ml). The yellow solution was concentrated to dryness, dissolved in CHCl$_3$, washed with saturated Na$_2$CO$_3$ solution and water. The organic layer was separated, dried (MgSO$_4$) and concentrated. Flash column chromatography (10% EtOH/CHCl$_3$, R$_f$=0.30) afforded the N$_\epsilon$-benzyl-N$_\alpha$-BOC-L-lysine t-butyl ester (24) (16.16 g, 54%) as a colorless oil. $^1$H NMR (CD$_3$OD) δ7.34–7.20 (m, 5H), 3.91 (dd, 1H, J=9.0, 5.1 Hz), 3.72 (s, 2H), 2.58 (t, 2H, J=7.2 Hz), 1.82–1.30 (m, 6H), 1.45 (s, 9H), 1.43 (s, 9H); $^{13}$C NMR (CDCl$_3$) δ171.9, 155.3, 140.1, 128.3, 128.1, 126.9, 81.6, 79.5, 53.9, 48.9, 32.7, 29.5, 28.3, 27.9, 22.9. HRMS m/z calcd. for C$_{22}$H$_{36}$N$_2$O$_4$ 392.2675, found 392.2676. Anal. calcd. for C$_{22}$H$_{35}$N$_2$O$_4$: C, 67.32; H, 9.24; N, 7.14. Found: C, 67.40; H, 9.28; N, 7.16. [α]$^{25}_D$ +6.9° (c=1.00, CDCl$_3$).

EXAMPLE 12

(2S, 9S)-7-Benzyl-2-[(tert-butoxycarbonyl)amino]-10-chloro-9-hydroxy-7-azadecanoic Acid, tert-Butyl Ester (25)

A mixture of N$_\epsilon$-benzyl-N$_\alpha$-BOC-L-lysine t-butyl ester (24) (16.0 g, 40.76 mmol), CH$_3$OH (40 ml), (S)-(+)-epichlorohydrin (4.17 g, 45.0 mmol) and anhydrous MgSO$_4$ (5.33 g. 44.28 mmol) was stirred under N$_2$ for three days. The solids were filtered off and washed with CH$_3$OH. The filtrate was concentrated at room temperature to give a yellow oil. The resulting oil was purified by flash chromatography on silica gel (66% hexane/ethyl acetate) to give 13.23 g of (25) (77%) as a colorless oil. $^1$H NMR (C$_6$D$_6$) δ7.18 (m, 5H), 5.00 (br d, 1H), 4.40 (m, 1H), 3.62 (m, 1H), 3.40–3.10 (m, 4H), 2.20–2.00 (m, 4H), 1.63 (m, 1H), 1.40 (s, 9H), 1.31 (s, 9H), 1.20 (m, 2H). $^{13}$C NMR (C$_6$D$_6$) δ171.7, 155.2, 138.8, 128.8, 127.9, 127.0, 80.8, 78.8, 67.7, 58.8, 57.2, 53.9, 53.7, 47.3, 32.5, 28.0, 27.5, 26.3, 22.8. HRMS m/z calcd. for C$_{25}$H$_{42}$ClN$_2$O$_5$ 485.2782, found 485.2775. [α]$^{25}_D$ +5.3° (c=1.00, CHCl$_3$).

EXAMPLE 13

(2S, 9R)-7-Benzyl-2-[(tert-butoxycarbonyl)amino]-10-cyano-9-hydroxy-7-azadecanoic Acid tert-Butyl Ester (26)

A mixture of (25) (6.99 g, 14.4 mmol), dry KCN (9.38 g, 144 mmol) and 18-crown-6 (0.76 g, 2.88 mmol) in 275 ml of dry acetonitrile was stirred at 45° C. for 5 days. It should be noted that heating this mixture to reflux causes significant decomposition. The reaction mixture was cooled, filtered and concentrated. Flash column chromatography on silica gel (25% ethyl acetate/hexane) gave the (2S, 9R)-nitrile (26) as a colorless oil (4.82 g, 70%). $^1$H NMR (CD$_3$OD) δ7.34–7.18 (m, 5H), 3.97–3.83 (m, 2H), 3.67 (dd, 1H, J=13.4, 2.6 Hz), 3.54 (dd, 1H, J=13.4, 4.0 Hz), 2.72–2.40 (m, 6H), 1.80–1.50 (m, 4H), 1.45 (s, 9H), 1.44 (s, 9H), 1.40–1.30 (m, 2H). $^{13}$C NMR (CDCl$_3$) δ171.8, 155.3, 138.1, 128.8, 128.4, 127.3, 117.1, 81.6, 79.5, 63.6, 58.8, 54.0, 32.6, 28.2, 27.9, 22.1. HRMS m/z calcd. for C$_{26}$H$_{42}$N$_3$O$_5$ 476.3124, found 476.3121. Anal. calcd. for C$_{26}$H$_{41}$N$_3$O$_5$: C, 65.66; H, 8.69; N, 8.83. Found: C, 65.71; H, 8.67; N, 8.80. [α]$^{25}_D$ +4.7° (c=1.00, CHCl$_3$).

EXAMPLE 14

(2S, 9R)-2-[(tert-Butoxycarbonyl)amino]-11-amino-9-hydroxy-7-azaundecanoic Acid tert-Butyl Ester, Diacetate Salt (27)

The N$_\epsilon$benzyl nitrile (26) (4.80 g, 10.7 mmol) was dissolved in glacial acetic acid (100 ml); 10% Pd—C (0.50 g) and PtO$_2$ (1.00 g) were added; and hydrogen gas was introduced. The reaction was complete after 6 hours, and the catalyst was filtered through a bed of Celite and washed with acetic acid. The filtrate was concentrated in vacuo. Azeotropic removal of the acetic acid with toluene gave (27) as a colorless oil (5.10 g, 99%) $_1$H NMR (500 MHz) (CD3OD) d 4.02–3.94 (m, 2H), 3.14–2.86 (m, 6H), 1.94 (s, 6H), 1.87–1.58 (m, 8H), 1.46 (s, 9H), 1.44 (s, 9H). $^{13}$C NMR (CD$_3$OD) δ169.6, 156.54, 85.3, 70.2, 62.6, 56.6, 54.2, 53.9, 34.0, 31.1, 28.2, 26.3, 23.2. HRMS m/z calcd. for C$_{19}$H$_{40}$N$_3$O$_5$ 390.2968, found 390.2977. [α]$^{25}_D$ +0.6° (c=1.00, CH$_3$OH).

EXAMPLE 15

(2S, 9R)-11-[(Benzyloxycarbonyl)amino]-2-[(tert-butoxycarbonyl)amino]-9-hydroxy-7-carbobenzyloxy-7-azaundecanoic Acid tert-Butyl Ester (28)

A solution of (27) (1.17 g, 2.30 mmol) in CHCl$_3$ (100 ml) was washed with saturated Na$_2$CO$_3$ solution. The aqueous layer was extracted with CHCl$_3$ (3×100 ml) and the combined organic layers were dried over Na$_2$SO$_4$ and concentrated in vacuo. A solution of the resultant oil (the free amine, 0.85 g, 2.18 mmol) in CH$_2$Cl$_2$ (60 ml) was cooled to 0° C. and treated with diisopropylethylamine (0.59 g, 4.57 mmol) and benzyl chloroformate (0.79 g, 4.60 mmol). The reaction mixture was stirred overnight at room temperature, concentrated to dryness and purified by flash chromatography (50% ethyl acetate/hexane) to give (28) (790 mg, 55%) as a colorless oil. $^1$H NMR (CDCl$_3$) δ7.23 (m, 10H), 5.45 (m, 1H), 5.08 (s, 2H), 5.04 (s, 2H), 4.10 (m, 1H), 3.80 (m, 1H), 3.40 (m, 1H), 3.23 (m, 5H), 1.80–1.43 (m, 6H), 1.41 (s, 18H), 1.23 (m, 2H); $^{13}$C NMR (CDCl$_3$) δ171.8, 157.5, 156.9, 155.3, 136.4, 128.4, 128.3, 127.9, 127.7, 81.6, 79.5, 69.2, 67.2, 66.5, 53.7, 48.5, 37.7, 34.8, 32.5, 28.2, 27.9, 22.3. HRMS m/z calcd. for C$_{35}$H$_{52}$N$_3$O$_9$ 658.3703, found 658.3774. [α]$^{24}_D$ +4.6° (c=0.50, CHCl$_3$).

EXAMPLE 16

(2S, 9R)-11-[(Benzyloxycarbonyl)amino]-7-(carbobenzyloxy)-9-hydroxy-7-azaundecanoic Acid (29)

The ester (28) (500 mg, 0.76 mmol) was dissolved in a pre-made mixture of trifluoroacetic acid (1.12 g, 9.90 mmol), $CH_2Cl_2$ (2.05 g, 24.0 mmol) and triethylsilane (220 mg, 1.9 mmol) and stirred at room temperature for 20 hours. The reaction mixture was concentrated to dryness and stirred again in the pre-made mixture as described above for an additional 6 hours. The reaction mixture was concentrated and the resultant oil dissolved in 1.0 ml water and adjusted to pH 8 with saturated $NaHCO_3$ solution. The solution was concentrated and purified by chromatography on a C-18 column (55% acetone/water) to give 300 mg (78%) of (29) as a colorless oil. $^1$H NMR ($CD_3OD$) δ7.40–7.25 (m, 10H), 5.11 (s, 2H), 5.06 (s, 2H), 3.82 (m, 1H), 3.55 (m, 1H), 3.40–3.10 (m, 6H), 1.95–1.30 (m, 8H). HRMS m/z calcd. for $C_{26}H_{36}N_3O_7$ 502.2553, found 502.2531. $[\alpha]^{24}_D$+4.2° (c=1.00, $CH_3OH$).

EXAMPLE 17

(2S, 9R)-2-Amino-11-[(Benzyloxycarbonyl)amino]-7-(carbobenzyloxy)-9-(tetrahydropyran-2-yloxy)-7-azaundecanoic Acid (30)

Trifluoroacetic acid (115 mg, 1.01 mmol) was added to a solution of (29) (265 mg, 0.53 mmol) in $CHCl_3$ (5 ml). The solution was concentrated in vacuo. The resultant oil was dissolved in dry $CH_2Cl_2$ (15 ml) and 3,4-dihydro-2H-pyran (51 mg, 55 μl, 0.61 mmol) was added at room temperature. The reaction progress was monitored by TLC and three additional portions of 3,4-dihydro-2H-pyran (51 mg each) were added over the next 7 hours. The reaction mixture was stirred for an additional 12 hours and concentrated in vacuo. The oil was dissolved in water and methanol (1:1, 4 ml) and adjusted to pH 7 with saturated $NaHCO_3$ solution. The solution was concentrated and the crude oil purified by chromatography on a C-18 column (55% acetone/water) to give 210 mg (68%) of (30) as a colorless oil and 20 mg (8%) recovered starting material (29). $^1$H NMR ($CD_3OD$) δ7.40–7.22 (m, 10H), 5.10 (m, 2H), 5.04 (s, 2H), 4.62–4.32 (m, 1H), 4.02–3.68 (m, 2H), 3.50 (m, 1H), 3.44–3.06 (m, 7H), 1.98–1.28 (m, 14H); $^{13}$C NMR ($CD_3OD$) δ174.3, 158.7, 158.1, 138.5, 129.7, 129.6, 129.5, 129.3, 129.0, 128.8, 101.7, 100.1, 74.9, 68.3, 67.4, 65.3, 56.2, 48.4, 38.2, 34.3, 32.6, 32.1, 28.5, 26.4, 23.6, 21.8, 21.2. HRMS m/z calcd. for $C_{31}H_{43}N_2O_8$ 586.3128, found 586.3118. $[\alpha]^{24}_D$+4.0° (c=0.25, $CH_3OH$).

EXAMPLE 18

Sodium (2S, 9R)-11-[(Benzyloxycarbonyl)amino]-7-(carbobenzyloxy)-2-[(9-fluorenylmethoxycarbonyl)amino]-9-(tetrahydropyran-2-yloxy)-7-azaundecanoic Acid (31)

A solution of 9-fluorenylmethyl N-succinimidyl carbonate (181 mg, 0.53 mmol) in DMF (2.5 ml) was added to a solution of (30) (210 mg, 0.36 mmol) in 9% $Na_2CO_3$ (0.836 ml, 0.72 mmol) at 0° C. and stirred overnight at room temperature. The pH was adjusted to 7 with 0.1 N HCl. The mixture was concentrated to an oil and purified by flash chromatography (90% $CHCl_3$/MeOH) to give (31) (239 mg, 83%) as a colorless oil. $^1$H NMR ($CDCl_3$) δ7.78 (m, 2H), 7.60 (m, 2H), 7.30 (m, 14H), 5.72 (m, 2H), 5.18 (s, 2H), 5.16 (s, 2H), 4.60 (m, 1H), 4.52–4.22 (m, 3H), 4.20 (m, 1H), 4.00–3.72 (m, 3H), 3.50–3.10 (m, 6H), 2.00–1.22 (m, 14H); $^{13}$C NMR (150 MHz) ($CDCl_3$) δ174.6, 156.7, 156.4, 143.9, 143.8, 141.3, 136.8, 136.5, 128.5, 128.5, 128.1, 128.0, 127.9, 127.7, 127.1, 125.1, 124.9, 120.0, 100.7, 73.5, 67.4, 67.2, 66.6, 53.5, 48.4, 47.2, 32.9, 32.0, 31.5, 30.8, 28.0, 27.3, 25.2, 22.0, 21.1, 19.8. HRMS m/z calcd. for $C_{46}H_{53}N_3O_{10}Na$ 830.3629, found 830.3661. Anal. calcd. for $C_{46}H_{53}N_3O_{10}$: C, 68.38; H, 6.61; N, 5.20. Found: C, 68.55; H, 6.63; N, 5.26. $[\alpha]^{26}_D$+3.4° (c=1.00, $CHCl_3$).

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A synthetic peptide containing a hypusine moiety having the formula selected from the group consisting of:

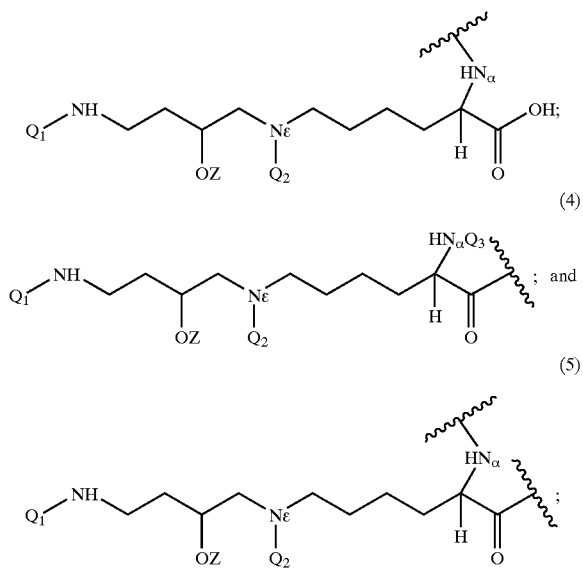

wherein:

$Q_1$ and $Q_2$ may be the same or different and are amino protective groups;

$Q_3$ is an amino protective group which is orthogonal to the amino protective groups $Q_1$ and $Q_2$; Z is a hydroxy protective group; and amide bond formation occurs at the alpha-amino group, and/or the alpha-carboxyl group.

2. The synthetic peptide of claim 1 wherein the absolute configuration of the carbon atoms at the 2-position and the 9-position, respectively, of the hypusine moiety is selected from the group consisting of (2R, 9S), (2S, 9S) and (2R, 9R).

3. The synthetic peptide according to claim 1 comprising the hexapeptide:

L-CYS-L-THR-GLY-HPU-L-HIS-GLY (SEQ ID NO: 3).

4. The synthetic peptide of claim 3 wherein the absolute configuration of the carbon atoms at the 2-position and the 9-position, respectively, of the hypusine moiety is selected from the group consisting of (2R, 9S), (2S, 9S) and (2R, 9R).

5. The synthetic peptide of claim 3 wherein the absolute configuration of the carbon atoms at the 2-position and the 9-position, respectively, of the hypusine moiety is 2S, 9R.

6. The synthetic peptide according to claim 1 comprising the pentapeptide:

L-THR-GLY-HPU-L-HIS-GLY (SEQ ID NO: 4).

7. The pentapeptide of claim 6 wherein the absolute configuration of the carbon atoms at the 2-position and the 9-position, respectively, of the hypusine moiety is selected from the group consisting of (2R, 9S), (2S, 9S) and (2R, 9R).

8. The pentapeptide of claim 6 wherein the absolute configuration of the carbon atoms at the 2-position and the 9-position, respectively, of the hypusine moiety is 2S, 9R.

9. The synthetic peptide of claim 1 wherein the absolute configuration of the carbon atoms at the 2-position and the 9-position, respectively, of the hypusine moiety is 2S, 9R.

10. The synthetic peptide of claim 1 wherein Z is tetrahydropyranyl.

11. The synthetic peptide of claim 1 wherein $Q_3$ and $Q_2$ are benzylcarboxy, $Q_1$ is fluorenylmethoxycarbonyl, and Z is tetrahydropyranyl.

12. The synthetic peptide of claim 1 wherein $Q_3$ and $Q_2$ are selected from the group consisting of benzylcarboxy, carbobenzyloxy (CBZ), tert-butoxycarbonyl (t-BOC), and tosyl.

13. The synthetic peptide of claim 12, wherein $Q_3$ and $Q_2$ are the same.

14. The synthetic peptide of claim 1 wherein $Q_1$ is fluorenylmethoxycarbonyl.

* * * * *